US010369554B2

(12) United States Patent
Mauer et al.

(10) Patent No.: US 10,369,554 B2
(45) Date of Patent: Aug. 6, 2019

(54) CATALYST COMPOSITION, ITS PREPARATION AND PROCESS USING SUCH COMPOSITION

(71) Applicant: SHELL OIL COMPANY, Houston, TX (US)

(72) Inventors: Richard Berend Mauer, Amsterdam (NL); Hong-Xin Li, Lansdale, PA (US); Gisela Sabater Pujadas, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/061,993

(22) PCT Filed: Dec. 15, 2016

(86) PCT No.: PCT/EP2016/081197
§ 371 (c)(1),
(2) Date: Jun. 13, 2018

(87) PCT Pub. No.: WO2017/102948
PCT Pub. Date: Jun. 22, 2017

(65) Prior Publication Data
US 2018/0369795 A1 Dec. 27, 2018

(30) Foreign Application Priority Data
Dec. 17, 2015 (EP) .................. 15200915

(51) Int. Cl.
*B01J 29/06* (2006.01)
*B01J 29/22* (2006.01)
*B01J 29/40* (2006.01)
*B01J 29/18* (2006.01)
*B01J 35/00* (2006.01)
*B01J 37/02* (2006.01)
*B01J 37/30* (2006.01)
*B01J 29/44* (2006.01)
*B01J 29/80* (2006.01)
*B01J 35/02* (2006.01)
*B01J 37/00* (2006.01)
*C07C 4/18* (2006.01)
*C07C 5/27* (2006.01)
*C07C 6/12* (2006.01)
*C07C 15/04* (2006.01)
*C07C 15/08* (2006.01)

(52) U.S. Cl.
CPC ............ *B01J 29/22* (2013.01); *B01J 29/185* (2013.01); *B01J 29/405* (2013.01); *B01J 29/44* (2013.01); *B01J 29/80* (2013.01); *B01J 35/0006* (2013.01); *B01J 35/023* (2013.01); *B01J 37/0009* (2013.01); *B01J 37/0201* (2013.01); *B01J 37/30* (2013.01); *C07C 4/18* (2013.01); *C07C 5/2737* (2013.01); *C07C 6/126* (2013.01); *C07C 15/04* (2013.01); *C07C 15/08* (2013.01); *B01J 29/18* (2013.01); *B01J 29/40* (2013.01); *B01J 2229/186* (2013.01); *B01J 2229/20* (2013.01); *B01J 2229/42* (2013.01); *C07C 2529/18* (2013.01); *C07C 2529/22* (2013.01); *C07C 2529/40* (2013.01); *C07C 2529/44* (2013.01); *C07C 2529/80* (2013.01); *Y02P 20/52* (2015.11)

(58) Field of Classification Search
CPC ... B01J 29/44; B01J 29/80; B01J 29/22; B01J 29/405; B01J 29/18; B01J 29/40; B01J 29/185; B01J 35/0006; B01J 35/35; B01J 35/023; B01J 37/0009; B01J 37/0201; B01J 37/30; B01J 2229/20; B01J 2229/42; B01J 2229/186; C07C 4/18; C07C 5/2737; C07C 6/126; C07C 15/08; C07C 15/04; C07C 2529/22; C07C 2529/44; C07C 2529/80; Y02P 20/52
USPC ............... 502/64, 66, 67, 69, 71, 74, 77, 78; 585/470, 471, 475, 483, 486
See application file for complete search history.

(56) References Cited

U.S. PATENT DOCUMENTS

| 3,702,886 | A | 11/1972 | Argauer et al. | |
|---|---|---|---|---|
| 4,511,547 | A | 4/1985 | Iwayama et al. | |
| 8,071,828 | B2 * | 12/2011 | Cao ........................ | C07C 2/66 585/319 |
| 8,574,542 | B2 * | 11/2013 | Domokos ............... | B01J 29/40 423/700 |
| 9,029,283 | B2 * | 5/2015 | Berg-Slot .............. | B01J 23/626 502/60 |
| 2010/0249479 | A1 * | 9/2010 | Berg-Slot .............. | B01J 23/626 585/489 |

(Continued)

FOREIGN PATENT DOCUMENTS

| EP | 1447131 A1 | 8/2004 |
|---|---|---|
| WO | 0038834 A1 | 7/2000 |
| WO | 20090016141 A1 | 2/2009 |

OTHER PUBLICATIONS

International Search Report and Written Opinion received for PCT Patent Application No. PCT/EP2016/081197, dated Mar. 24, 2017, 9 pages.

(Continued)

*Primary Examiner* — Elizabeth D Wood
(74) *Attorney, Agent, or Firm* — Charles W. Stewart

(57) ABSTRACT

Catalyst composition comprising a carrier and one or more Group 10 metal components, wherein the carrier comprises (i) 20 to 90 wt % mordenite having a silica to alumina molar ratio in the range of from 10 to 60; (ii) 10 to 70 wt % ZSM-5 type zeolite having a silica to alumina molar ratio in the range of from 5 to 50 and an average particle size in the range of from 5 to 50 nm; and (iii) 10 to 50 wt % of binder; a process for preparing the catalyst, and a process for the conversion of an aromatic hydrocarbons-containing feedstock using the catalyst.

14 Claims, No Drawings

(56) References Cited

U.S. PATENT DOCUMENTS

2013/0197290 A1* 8/2013 Domokos ................ B01J 29/40
585/486
2013/0281757 A1* 10/2013 Domokos ................ B01J 29/40
585/489
2015/0217281 A1* 8/2015 Berg-Slot ............... B01J 23/626
585/489

OTHER PUBLICATIONS

Baerlocher et al., Atlas of Zeolite Framework Types, Sixth Revised Edition, 2007, 6 pages.

* cited by examiner

US 10,369,554 B2

CATALYST COMPOSITION, ITS PREPARATION AND PROCESS USING SUCH COMPOSITION

CROSS REFERENCE TO RELATED APPLICATIONS

This is a national stage application of International Application No. PCT/EP2016/081197, filed 15 Dec. 2016, which claims benefit of priority to European Application No. 15200915.5, filed 17 Dec. 2015.

FIELD OF THE INVENTION

The present invention relates to a catalyst composition, a process for preparing the catalyst and a process for the conversion of an aromatic hydrocarbons containing feedstock using the catalyst.

BACKGROUND OF THE INVENTION

Each benzene and para-xylene are industrially important starting materials. Benzene is for instance widely used as a feed to make cyclohexane which in turn can be used to make nylons, whereas para-xylene is used for the production of for example polyester fibers.

Para-xylene is derivable from a xylene mixture which in addition contains the isomers meta-xylene and ortho-xylene. Of the xylene isomers para-xylene is the most in demand, whereas ortho-xylene and meta-xylene are much less in demand. Thus, it is industrially important to convert ortho-xylene and meta-xylene into para-xylene.

Xylene mixtures are usually obtained by subjecting naphtha to a reforming process which is followed by aromatic extraction. The xylene mixtures can also contain cracked xylenes which have been obtained by subjecting naphtha to a thermal decomposition treatment, followed by aromatic extraction. In addition to the xylene isomers such xylene mixtures also contain high concentrations of ethylbenzene and non-aromatic hydrocarbons such as cyclic aliphatics.

Much research and development work has been directed to processes and catalysts to convert such xylene mixtures into mixtures that contain a high amount of benzene, as well as a high amount of para-xylene. In such conversion processes dealkylation of ethylbenzene mainly into benzene is established, and at the same time isomerization of ortho-xylene and/or meta-xylene into para-xylene.

A difficulty that arises in such xylene mixture conversion processes is the presence of so-called benzene co-boilers. Benzene co-boilers are non-aromatic hydrocarbon impurities such as cyclohexane and methylcyclopentane that are very difficult to separate from benzene by distillation because they have a boiling point close to that of benzene. Since benzene as a starting material needs to meet stringent purity standards these benzene co-boilers need to be removed by means of an additional extraction step which is expensive and time-consuming.

Another difficulty is that individual isomers of xylene and ethylbenzene are close in their boiling point, making it very difficult to separate para-xylene from ethylbenzene by distillation.

Alkylaromatic conversion catalysts have been described in WO0038834 and WO2009016134.

SUMMARY OF THE INVENTION

An object of the invention is to produce benzene of improved purity. Improved purity can make that the product obtained contains less compounds having a boiling point in the boiling point range of benzene. It may further be advantageous if the benzene is obtained in high yield. A further object can be to obtain para-xylene in high yield. Additionally, it can be preferred that only a limited amount of aromatic compounds is lost in the aromatic hydrocarbon conversion process.

The present invention relates to a catalyst composition which comprises a carrier and one or more metal components supported on the carrier, wherein the carrier comprises (i) mordenite in an amount in the range of from 20 to 90% by weight (wt %), based on total weight of carrier, the mordenite having a silica to alumina molar ratio in the range of from 10 to 60; (ii) ZSM-5 type zeolite in an amount of from 10 to 70 wt %, based on total weight of carrier, the ZSM-5 type zeolite having a silica to alumina molar ratio in the range of from 5 to 50 and a number average particle size in the range of from 5 to 50 nm; and (iii) an inorganic binder in an amount in the range of from 10 to 50 wt %, based on total weight of carrier; and wherein the one or more metal components comprise a group 10 metal.

Each mordenite and ZSM-5 are as defined in the Atlas of Zeolite Framework Types, sixth revised edition 2007.

The bulk or overall SAR can be determined by any one of a number of chemical analysis techniques. Such techniques include X-ray fluorescence, atomic adsorption, and inductive coupled plasma-atomic emission spectroscopy (ICP-AES). All will provide substantially the same bulk ratio value. The silica to alumina molar ratio for use in the present invention is determined by X-ray fluorescence.

Use of the present catalyst in a process for conversion, more specifically transalkylation, of an aromatic hydrocarbons-containing feedstock has enabled the production of high purity benzene.

DETAILED DESCRIPTION OF THE INVENTION

The catalyst composition according to the present invention comprises a carrier which comprises mordenite in an amount of from 20 to 90 wt %, based on total weight of carrier. Preferably, the mordenite is present in an amount in the range of from 30 to 70 wt %, more preferably in the range of from 40 to 60 wt %, based on total weight of carrier.

The mordenite has a silica to alumina molar ratio in the range of from 10 to 60. The mordenite has preferably a silica to alumina molar ratio in the range of from 15 to 40, more preferably in the range of from 15 to 25.

Preferably, the mordenite contains less than 400 ppm of transition metals, more preferably less than 300 ppm of transition metals. Transition metals are metals in the so-called d-block of the IUPAC Periodic Table. These metals are the elements of groups 3 to 12 of this periodic table. In particular, the mordenite contains less than 250 ppm of iron, more preferably less than 100 ppm of iron. Suitable mordenite has been described in EP1447131 more specifically Example 9 of EP1447131.

The present catalyst composition comprises a carrier which comprises a ZSM-5 type zeolite in an amount of 10 to 70 wt %, based on total weight of carrier material compound. Preferably, the ZSM-5 type zeolite is present in an amount in the range of from 15 to 60 wt %, more preferably in the range of from 20 to 40 wt %, based on total weight of carrier.

The ZSM-5 type zeolite has a silica to alumina molar ratio in the range of from 10 to 50, preferably in the range of 20 to 40, and more preferably in the range of from 23 to 35.

The ZSM-5 type zeolite has a number average particle size in the range of 5 to 50 nm. The average particle size is determined by calculating the number average particle size of a sample which has been measured by Transmission Electron Microscopy (TEM). Preferably, the ZSM-5 type zeolite has a number average particle size in the range of from 10 to 45 nm, more preferably in the range of from 20 to 40 nm. It has been found that the small average particle of the ZSM-5 type zeolite used in accordance with the present invention improves both the benzene purity and the selectivity towards para-xylene.

Suitable ZSM-5 type zeolites to be used in accordance with the present invention can be prepared as for example described in U.S. Pat. Nos. 3,702,886 and 4,511,547. Suitable examples of ZSM-5 type zeolites include CBV 3014E, CBV 3020E and CBV 8014, available commercially from Zeolyst International.

The catalyst according to the present invention also contains an inorganic binder in an amount in the range of from 5 to 50 wt %, based on total weight of carrier. Preferably, the inorganic binder is present in an amount in the range of from 10 to 40 wt %, more preferably in the range of from 15 to 30 wt %, based on total carrier.

Suitably, the inorganic binder is selected from the group consisting of gamma-alumina, silica, silica-alumina, bentonite, kaolin, titania, zirconia, ceria, Gallia, climotilolite, montmorillonite, and any mixture thereof. Prefered inorganic binder include amorphous inorganic oxides of gamma alumina, silica and silica alumina. More preferred inorganic binders include gamma alumina and silica.

In shaped form, for example as extrudates, the carrier generally has a surface area falling in the range of from 200 to 600 $m^2/g$, preferably 250 to 500 $m^2/g$, more preferably from 350 to 450 $m^2/g$; and a pore volume, by mercury intrusion, in the range of from 0.2 to 1.2 ml/g, preferably 0.4 to 1.0 ml/g, more preferably 0.5 to 0.8 ml/g.

The present catalyst composition may be shaped in any particular form. Suitable shapes include trilobes and cylinders, Preferably, the present catalyst composition is in the shape of trilobes.

The present catalyst comprises one or more metal components from the group 10 metals preferably in an amount in the range of from 0.005 to 10 wt %, based on total weight of catalyst.

The amount is the amount of metal on total weight of catalyst. Reference to group 10 as used herein relates to the current IUPAC version of the Periodic Table. Preferred catalytically active metals are nickel, palladium and/or platinum. The most preferred metal is platinum. Combinations of two or more catalytically active metals are also possible, preferably being metal combinations comprising platinum. The catalytically active metal may also be provided in the form of a compound, optionally requiring activation before use.

Preferably, the present catalyst comprises the group 10 metal, preferably platinum, in an amount in the range of from 0.005 to 10 wt %, more preferably in the range of from 0.01 to 5 wt %, more preferably of from 0.01 to 1 wt %, based on total weight of catalyst.

The catalyst composition according to the invention can suitably have such shape that a reactor filled with the catalyst particles has an average void fraction of at least 10% by volume, preferably in the range of from 20 to 70%, more preferably in the range of from 35 to 55% by volume.

The catalyst composition of the present invention may be prepared using standard techniques for combining the carriers and include shaping; compositing with the metals components; and any subsequent useful process steps such as drying, calcining, and reducing.

The present invention also relates to a process for preparing the catalyst according to the present invention, comprising the steps of:
(a) mixing the mordenite, ZSM-5 type zeolite, inorganic binder, and group 10 metal, preferably platinum, in any possible sequence; and
(b) calcining the mixture as obtained in step (a).

Each the mordenite and the ZSM-5 zeolite for use in this process preferably are as described above for the catalyst composition.

In a particular embodiment, the catalyst composition is obtained by preparing the carrier and subsequently incorporating one or more metal components. The carrier can be prepared by shaping the carrier, optionally drying the shaped carrier, and subsequently calcining. Drying temperatures can suitably be in the range of from 50 to 200° C. Drying times can suitably be in the range of from 0.5 to 24 hours. Calcination temperatures can suitably be in the range of from 200 to 800° C., preferably in the range of from 300 to 600° C. The calcination of the material, a relatively short time can suitably be applied in the range of from 0.5 to 5 hours. The calcinations can suitably be carried out at a temperature in the range of from 400 to 700° C., preferably in the range of from 450 to 600° C.

In step (b), the calcining can suitably carried out at a temperature above 450° C., preferably above 500° C.

The group 10 metal is suitably incorporated in the carrier with the help of a group 10 metal salt solution. The metal salt solution suitably has a pH in the range of from 1 to 12. The metal salts that can suitably be used include chloroplatinic acid and ammonium stabilised metal salts. If present, an additional metal can suitably be added in the form of water soluble organic or inorganic salt in solution. Examples of suitable salts are nitrates, sulphates, hydroxides and ammonium (amine) complexes.

The metals may be impregnated either sequentially or simultaneously. It is preferable that the metals be added simultaneously. Suitably, a complexing agent or chelating agent is used in a combined bimetallic salt solution to prevent unwanted metals precipitation. Examples of suitable complexing agents include EDTA (ethlyenediaminetetraacetic acid), and derivatives thereof; HEDTA (N-(2-hydroxyethyl)ethylenediamine-N,N',N'-triacetic acid), EGTA (ethylene glycol-bis(2-aminoethylether)-N,N,N',N'-tetraacetic acid), DTPA (diethylene tridiamine pentaacetic acid), and NTA (nitrilotriacetic acid).

Before use of the catalyst composition, it will be preferred that the metals on the catalyst composition are in metallic (and not oxidic) form. Accordingly, the catalyst composition preferably is subjected to reducing conditions, which are, for example, heating in a reducing atmosphere, such as in hydrogen optionally diluted by an inert gas, such as nitrogen or carbon dioxide, at temperature in the range of from 150 to 600° C. for a period of time in the range from 0.5 to 5 hours.

The present invention also relates to a process for the conversion, more specifically transalkylation, of an aromatic hydrocarbons-containing feedstock using a catalyst in accordance with the present invention. Suitably, the aromatic hydrocarbons comprise benzene, toluene and/or aromatics containing at least 9 carbon atoms.

The aromatic hydrocarbons-containing feedstock suitably includes materials for producing para-xylene such as C8 aromatic hydrocarbon mixtures obtained by reforming naphtha and the subsequent extraction and/or fractionation; C8 aromatic hydrocarbon mixtures obtained by reforming naphtha but not undergoing processes for extracting naphthene and paraffin to contain naphthene and paraffin having the carbon number of around 9; and C8 aromatic hydrocarbon mixtures obtained through extraction and/or fraction of cracked gasoline which is produced as a by-product of thermal decomposition of naphtha.

The feedstock that contains the aromatic hydrocarbons to be transalkylated suitable comprises C7 to C9 hydrocarbons, and in particular one or more of ortho-xylene, meta-xylene, para-xylene, toluene, and benzene in addition to ethylbenzene. Generally the amount of ethylbenzene in the feedstock is in the range of from 0.1 to 50 wt % and the total xylene content is typically at least 20 wt %, all based on total amount of feedstock. Typically the xylenes will not be in a thermodynamic equilibrium, and the amount of para-xylene will be lower than that of the other xylene isomers.

The feedstock suitably is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The present transalkylation process preferably is carried out at a temperature in the range of from 200 to 600° C., preferably in the range of from 250 to 500° C., and more preferably in the range of from 300 to 400C°.

The process is carried out at a pressure in the range of from 5 to 50 bara, preferably at a pressure in the range of from 10 to 40 bara, and more preferably at a pressure in the range of from 25 to 35 bara.

The weight space velocity applied in the process is suitably in the range of from 0.2 to 30 $hr^{-1}$, preferably from 2 to 20 $hr^{-1}$, and more preferably in the range of from 3 to 6 $hr^{-1}$.

The feed to hydrogen ratio $mol.mol^1$ is in the range of from 0.5 to 100, preferably in the range of from 1 to 10.

The reaction effluent preferably will be recovered and subjected to a distillation treatment to remove the desired products, i.e., para-xylene and benzene. Unreacted reactant such as for instance toluene can suitably be recycled for further reaction.

The present invention will now be illustrated by the following Examples.

EXAMPLE 1

A composition comprising 23 grams of mordenite (having a SAR of 20), 15 grams of ZSM-5 (having a SAR of 24 and an average particle size of between 35 and 50), and 8 g of alumina binder was mixed and peptized together with metal salt solution comprising tin and platinum. The amounts are based on total amount of dry composition. The peptized mixture was extruded to obtain particles having a diameter of 1.5 mm. These extrudates were dried at 120° C. for 2 hours followed by calcination in air of the sample at 550° C. for 2 hours. The composition is hereinafter referred to as Catalyst Composition A.

For comparison, a catalyst composition was prepared as described above but differing in that the ZSM-5 was a ZSM-5 having a SAR of 23 and an average particle size in the range of from 75 to 125 nm commercially available from Zeolyst International. The composition is hereinafter referred to as Catalyst Composition B.

EXAMPLE 2

A catalytic activity test was carried out that used a feed of which the composition is summarized in Table 1.

TABLE 1

| Component | Content (wt %) |
|---|---|
| Toluene | 50.5 |
| Trimethylbenzenes | 28.6 |
| Ethyltoluenes | 11 |
| Propylbenzenes | 0.8 |
| Indane | 1.4 |
| Ethylxylenes | 7 |
| Tetramethylbenzenes | 0.5 |
| Remainder including compounds containing at least 10 carbon atoms + rest | 0.3 |

The activity test was performed once the catalyst compositions were converted into their reduced state, which was achieved by exposing the dried and calcined Catalyst Compositions A and B to atmospheric hydrogen (>99% purity) at 400° C. for 1 hour. The catalysts obtained are referred to as Catalyst A and Catalyst B, respectively.

In the present case, a weight hourly space velocity of 3.0 g feed/g catalyst/hour, hydrogen to feed ratio of 4.5 mol-.$mol^{-1}$ and a total system pressure of 30 bar was used in a fixed bed reactor. The temperature was varied to achieve the required conversion of 45%.

The performance characteristics are shown in Table 2 below.

The purity of the benzene is given as the amount of benzene in the fraction boiling in the benzene boiling range in the product. This fraction will contain compounds containing 6 carbon atoms such as benzene, methyl substituted cyclic compounds containing 5 carbons and cyclic compounds containing 6 carbon atoms.

The aromatic loss is calculated as the wt % aromatic compounds in the feed minus the wt % aromatic compounds in the product divided by the wt % aromatic compounds in the feed. This amount is given relative to the aromatic loss when using Catalyst B.

TABLE 2

| | Catalyst A | Catalyst B (Comparative) |
|---|---|---|
| Relative percentage of co-boilers | 19 | 43 |
| Relative aromatic losses (%) | 78.95 | 100 |

The above experimental results show that catalysts according to the present invention allow obtaining product having increased benzene purity. Furthermore, it was possible to reduce the loss of aromatic compounds.

That which is claimed is:

1. A catalyst composition which comprises a carrier and one or more metal components supported on the carrier, wherein the carrier comprises (i) mordenite in an amount in the range of from 20 to 90 wt %, based on total weight of carrier, the mordenite having a silica to alumina molar ratio in the range of from 10 to 60; (ii) ZSM-5 type zeolite in an amount of from 10 to 70 wt %, based on total weight of carrier, the ZSM-5 type zeolite having a silica to alumina molar ratio in the range of from 5 to 50 and an average particle size in the range of from 5 to 50 nm; and (iii) an inorganic binder in an amount in the range of from 10 to 50 wt %, based on total weight of carrier; and wherein the one or more metal components comprise a group 10 metal.

2. The catalyst composition according to claim 1, wherein the mordenite is present in an amount in the range of from 30 to 70 wt %, based on total weight of carrier.

3. The catalyst composition according to claim 1, wherein the ZSM-5 type zeolite is present in an amount in the range of from 15 to 60 wt %, based on total weight of carrier.

4. The catalyst composition according to claim 1, wherein the inorganic binder is present in an amount in the range of from 10 to 40 wt %, based on total weight of carrier material.

5. The catalyst composition according to claim 1, wherein the ZSM-5 type zeolite has a number average particle size in the range of from 10 to 45 nm.

6. The catalyst composition according to claim 1, wherein the mordenite contains less than 200 ppm of transition metal(s).

7. The process for preparing the catalyst according to claim 1, comprising the steps of:
   (a) mixing the mordenite, ZSM-5 type zeolite, inorganic binder, and group 10 metal in any possible sequence; and
   (b) calcining the mixture as obtained in step (a).

8. A transalkylation process, wherein said process comprises: contacting an aromatic hydrocarbons-containing feedstock, wherein said feedstock comprises benzene, toluene and/or an aromatic containing at least 9 carbon atoms, with said catalyst composition recited in claim 1 and in the presence of hydrogen and at a temperature in the range of from 200 to 600° C., a pressure in the range of from 5 to 50 bara, and a weight space velocity in the range of from 0.2 to 30 hr$^{-1}$; and yielding a reaction effluent.

9. The process according to claim 8, wherein the feedstock comprises an amount of ethylbenzene in the range of from 0.1 to 50 wt % and a total xylene content of at least 20 wt %, all based on total amount of feedstock.

10. A transalkylation process, wherein said process comprises: contacting an aromatic hydrocarbons-containing feedstock, wherein said feedstock comprises benzene, toluene, and/or an aromatic containing at least 9 carbon atoms, with said catalyst composition recited in claim 2 and in the presence of hydrogen and at a temperature in the range of from 200 to 600° C., a pressure in the range of from 5 to 50 bara, and a weight space velocity in the range of from 0.2 to 30 hr$^{-1}$; and yielding a reaction effluent.

11. The transalkylation process according to claim 10, wherein the ZSM-5 type zeolite is present in an amount in the range of from 15 to 60 wt %, based on total weight of carrier.

12. The transalkylation process according to claim 11, wherein the inorganic binder is present in an amount in the range of from 10 to 40 wt %, based on total weight of carrier material.

13. The transalkylation process according to claim 12, wherein the ZSM-5 type zeolite has a number average particle size in the range of from 10 to 45 nm.

14. The transalkylation process according to claim 13, wherein the mordenite contains less than 200 ppm of transition metal(s).

* * * * *